(12) United States Patent
Senn et al.

(10) Patent No.: US 9,161,828 B2
(45) Date of Patent: Oct. 20, 2015

(54) APPARATUS FOR LIGHT-CURING A DENTAL OBJECT

(75) Inventors: Bruno Senn, Buchs (CH); Wolfgang Plank, Rankweil (AT); Gottfried Rohner, Altstätten (CH)

(73) Assignee: Ivoclar Vivadent AG, Schaan (LI)

( * ) Notice: Subject to any disclaimer, the term of this patent is extended or adjusted under 35 U.S.C. 154(b) by 492 days.

(21) Appl. No.: 12/454,482

(22) Filed: May 19, 2009

(65) Prior Publication Data

US 2010/0003633 A1    Jan. 7, 2010

(30) Foreign Application Priority Data

Jul. 1, 2008  (DE) .......................... 10 2008 031 094

(51) Int. Cl.
| | |
|---|---|
| A61C 19/00 | (2006.01) |
| A61C 13/15 | (2006.01) |
| G01B 11/02 | (2006.01) |
| G01J 1/42 | (2006.01) |
| G01N 21/55 | (2014.01) |

(52) U.S. Cl.
CPC ............. *A61C 19/004* (2013.01); *G01B 11/026* (2013.01); *G01J 1/4228* (2013.01); *G01N 21/55* (2013.01); *G01J 2001/4252* (2013.01); *G01N 2201/062* (2013.01)

(58) Field of Classification Search
CPC ...................................................... A61C 19/004
USPC ............................................................ 433/29
See application file for complete search history.

(56) References Cited

U.S. PATENT DOCUMENTS

| | | | |
|---|---|---|---|
| 5,487,662 A | | 1/1996 | Kipke |
| 5,738,678 A | * | 4/1998 | Patel ............................... 606/10 |
| 6,976,841 B1 | * | 12/2005 | Osterwalder ................... 433/29 |
| 7,245,371 B2 | * | 7/2007 | Wang et al. .................... 356/301 |
| 7,976,307 B2 | | 7/2011 | Plank et al. |
| 2003/0215767 A1 | * | 11/2003 | Taub et al. ...................... 433/29 |
| 2005/0003323 A1 | | 1/2005 | Kasuda et al. |
| 2005/0202363 A1 | * | 9/2005 | Osterwalder ................... 433/29 |
| 2006/0008787 A1 | | 1/2006 | Hayman |
| 2006/0199144 A1 | | 9/2006 | Liu et al. |
| 2007/0259309 A1 | * | 11/2007 | West et al. ...................... 433/29 |
| 2010/0140450 A1 | | 6/2010 | Duret et al. |

FOREIGN PATENT DOCUMENTS

| | | |
|---|---|---|
| DE | 101 07 099 A1 | 9/2002 |
| DE | 298 24 899 U1 | 7/2003 |
| EP | 0 678 282 A2 | 10/1995 |
| EP | 1 236 444 A1 * | 4/2002 |
| JP | 2004-159999 A | 6/2004 |
| JP | 2008-038155 A | 2/2008 |
| WO | WO 99/06871 | 2/1999 |
| WO | WO 02/33312 A2 | 4/2002 |
| WO | WO 2007/005022 A1 | 1/2007 |
| WO | 2008/068439 A1 | 6/2008 |

* cited by examiner

*Primary Examiner* — Ralph Lewis
(74) *Attorney, Agent, or Firm* — Ann M. Knab; Thad McMurray

(57) ABSTRACT

The invention relates to an apparatus for irradiating an object, in particular for light-curing a dental object by means of a first radiation, the apparatus comprising at least one radiation source for emitting the first radiation, the apparatus further comprising at least one radiation sensor for measuring at least a second radiation, and the apparatus further comprising a housing. The second radiation is the first radiation reelected by the object.

9 Claims, 3 Drawing Sheets

APPARATUS FOR LIGHT-CURING A DENTAL OBJECT

CROSS-REFERENCE TO RELATED APPLICATIONS

This application claims foreign priority benefits under 35 U.S.C. §119(a)-(d) from German patent application ser. no. P 10 2008 031 094.8 filed Jul. 1, 2008.

TECHNICAL FIELD

The invention relates to an apparatus for light-curing a dental object by means of a first radiation, wherein the apparatus is provided with a housing, at least one radiation source mounted on the housing for emitting the first radiation, and at least one radiation sensor mounted on the housing for measuring at least a second radiation, wherein the second radiation is the first radiation reflected by the object.

BACKGROUND OF THE INVENTION

For curing dental filling materials used for the purpose of restoration for natural teeth but also for separately fabricated sets of teeth, radiation with a high UV portion is employed.

Plastics are popular filling, materials that can be cured with electromagnetic radiation in material-dependent wavelength ranges (light). A precondition for an optimum polymerization of the plastic material is the introduction of a necessary amount of light, resulting from the light power times the exposure time.

When using light the operator precisely has to position the light source above the filling material. If the light is aimed next to the filling material, not enough light is fed to the filling material. This results in not providing the required amount of light in order to cure the filling material.

Conventional systems have orange filter glasses in order to support the positioning of the light source, which orange filter glasses subdue the light in such a manner that the spot is visible, for example in the mouth area, on which the light falls. The orange filter glasses, however, are tediously to handle and make the application of the light source complicated. Moreover, there are situations in which a determination of the correct positioning of the light source is not possible at all.

Modern dental treatment instruments that remove material from the tooth by means of a high-energy laser beam are capable of carrying out a position determination based on the plasma radiation resulting from the removal of material. In this conjunction, the intensity of the plasma radiation contains all information about the distance between tooth and dental treatment instrument. Based on this information, the dental treatment instrument can be switched off automatically if it is positioned too far away from the tooth.

When curing filling materials, however, there is no radiation by means of which it would possible to determine the radiation source.

OBJECTS AND SUMMARY OF THE INVENTION

Therefore, it is the object of the invention to provide an apparatus for irradiating or curing an object, to provide a treatment set for irradiating or curing an object, and to provide a method for irradiation or curing an object, by means of which the position of a radiation source can be determined more easily.

The invention is based on the concept that for determining the relative position of a radiation source with respect to an object, it is not necessarily required to have a radiation generated by the object. It is rather possible to make use of the radiation emitted from the radiation source and reflected by the object. Surprisingly, it has become apparent that the radiation of a radiation source when reflected by the object, is changed in a typical manner. This typical change enables a horizontal position determination of the radiation source since various objects are situated in the oral area of a patient, for example, that differ from the object that is impinged, and that change the radiation of the radiation source in their own typical manner.

In this way, for example, it can easily be checked if the radiation source is positioned above the filling material that is to be cured. Further, it is possible to determine by means of the run-time of the radiation or by means of the reflected light power measured, how far the radiation source is distant from the object.

According to the invention, a particular apparatus for irradiating an object by means of a first radiation that has at least one radiation source, is provided, wherein the radiation source of the apparatus emits the first radiation that is reflected by the object as a second radiation. In this case at least one radiation sensor detects the second radiation.

By means of detecting the radiation reflected by the object it is possible to visibly depict the same for the user of the apparatus. The advantage is that by means of the apparatus of the present invention it is possible to manually or automatically determine the position of the radiation source. When determining the position manually, on account of the radiation measured by the radiation sensor, it is possible for the user to tell in which way the radiation sensor and thus the apparatus are positioned relative to the object. With the automatic position determination, further improvements are possible, such as an automatic adjustment of the first radiation.

It is particularly expedient to apply the invention in the field of dental technology. In this case the radiation source irradiates or emits high-energy light for curing a dental filling material and is preferably embodied as a laser or light emitting diode. Most of the dental filling materials are represented brighter than Dentin in the short-wave blue light range. Therefore, the radiation sensor merely has to determine or ascertain whether the radiation that is reflected is very bright. This indicates that the radiation source is positioned above the filling material.

According to the invention it is particularly expedient it the radiation sensor is especially sensitive in a wavelength range that corresponds to the first radiation emitted from the radiation source. By means of this measure, the measuring range can already be limited by these technical means such that the technical realization of the apparatus is particularly simple.

According to the invention it is especially expedient if the inventive apparatus is provided with an output device for outputting information that is perceptible by the human being. The information can be for example images, sounds or vibrations. The information is generated based on the signals that are output by the radiation sensor.

According to the invention is is particularly expedient to detect the intensity of the second radiation. As has already been discussed, radiation with different characteristics is reflected by different objects. These characteristics can be the scattering or the degree of reflection, for example. The inventive apparatus enables to perform the position determination relative to the object that is irradiated, whereas it is possible to merely evaluate the intensity of the radiation that is reflected. On the one hand, the intensity directly provides information about the characteristics of the object itself since various objects reflect the first radiation of the radiation source with different intensities. The intensity, however, can also be taken from information on the distance between the radiation source and the object.

According to the invention is particularly favorable to use an output device that distinguishes the perceptible information based on a comparison with at least one reference value. In this case, the reference value is preferably a measured value that has been detected by the radiation sensor for a predetermined object. By means of the information distinguished, such as an optically particularly favorable output, a high sound, a vibration or any other distinguishing signaling, an user of the apparatus is immediately able to tell when the apparatus is situated above a desired object such as the tilling material. Therefore, the optimum position of the apparatus can immediately be recognized. Thus, especially for untrained users it is possible to avoid long initial training time since the apparatus is nearly self-explanatory.

According to the invention it is particularly expedient to use the measured values for adjusting the apparatus. In this case, the apparatus comprises an adjustment device that preferably determines the distance between radiation sensor and object based on the second radiation. Based on this distance the adjustment device can adjust the system parameters of the apparatus. Preferably, those parameters are the emitted light power and the on-time of the radiation source. Since the amount of light of a radiation source that is absorbed by the object, changes more in dependence on the distance from the object that is irradiated, this approach is particularly efficient in the reduction of losses. This not only saves energy and avoids unnecessary heating of the apparatus, but also ensures that the amount of light necessary to effect polymerization, is supplied to the object.

According to the invention it is particularly expedient to have a multiple arrangement of the radiation sensors. When curing a tooth filling material, the multiple arrangement can be embodied in hood shape in order to detect the irradiation of the filling material. In case the radiation sensor is received in such a multiple arrangement, the invention is particularly efficient since a hood-shaped multiple arrangement of light sources mostly blocks the unhindered sight or clear view of the object that is to be treated.

In a further advantageous embodiment it is provided that a radiation source is preferably formed by at least one laser diode or light emitting diode, whereas each light emitting diode at least comprises one LED-chip.

In a further advantageous embodiment it is provided that the radiation source and the at least one radiation sensor are arranged at the housing or are part of an attachment that is detachably mounted on the housing.

In a further advantageous embodiment it is provided that the radiation source emits a first radiation with a wavelength of 320 nm to 750 nm.

In a further advantageous embodiment it is provided that the radiation sensor is sensitive in a wavelength range of the first radiation emitted by the radiation source.

In a further advantageous embodiment it is provided that at least one of the radiation sensors is an image sensor by means of which at least one picture of the object can be taken.

In a further advantageous embodiment it is provided that one second or a plurality of radiation sensors are provided that are arranged in spaced apart relationship in the same plane and/or in angles relative to the radiation sensor.

In a further advantageous embodiment it is provided that the apparatus comprises an output device for outputting perceptible information.

In a further advantageous embodiment it is provided that the perceptible information is based on at least one measured value from at least one radiation sensor, the measured value in particular indicating the intensity of the second radiation or being compared to at least on reference value.

In a further advantageous embodiment it is provided that the output device is embodied as a display that is arranged at the apparatus and/or the output device outputs the information in a visual and/or acoustical and/or sensible manner.

In a further advantageous embodiment it is provided that the apparatus determines the distance to the reflection surface from the second radiation.

In a yet further advantageous embodiment there is provided an apparatus for indicating the radiation that is measured by at least one radiation sensor.

In a further advantageous embodiment it is provided that a charging station for charging and/or storing the apparatus is provided.

In a further advantageous embodiment the following steps are provided: irradiating the dental object by means of a radiation source; measuring the reflected radiation; and detecting a reflected radiation; and detecting a relative position of the radiation source with respect to the dental object based on the reflected light.

BRIEF DESCRIPTION OF THE FIGURES

Further advantages, details and features will become apparent from the following description of exemplary embodiments of the invention with reference to the drawings, in which.

DETAILED DESCRIPTION

As previously noted, it is a feature of this invention to provide an apparatus for irradiating an object by means of a first radiation from a radiation source, wherein the first radiation that is reflected by the object is a second radiation, the apparatus being provided with a sensor for detect the second radiation. The inventive apparatus and the object that is to be irradiated are embodied as a polymerization lamp and as a dental filling material in all preferred embodiments. The material of the filling is plastic material and soft at first. The plastic material used for the restoration process is cured by means of radiation that is a high-energy radiation with a comparably large spectral blue portion in the present embodiment.

Figure 1:
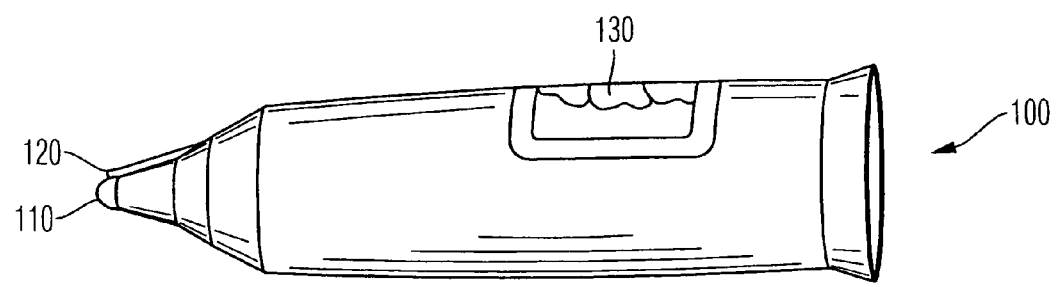
FIG. 1 shows a diagrammatic view of a first exemplary embodiment of the invention.

FIG. 1 shows a polymerization lamp 100 having a radiation source 110 and a radiation sensor 120.

The radiation source 110 is a light-emitting diode, in short LED 110 in all embodiments. However, this is not to be understood in a limiting sense, since also other suitable radiation sources such as halogen lamps, xenon lamps and laser diodes are known to a person skilled in the art. In operation, the LED 110 emits light with a high portion of blue light, by means of which the plastic material is irradiated and cured. The efficiency and through-curing of the filling material with the aid of the LED 110 depends crucially on the skill of the user. If the user exactly hits the plastic filling material with the light beam, the LED 110 has to emit less energy for the complete curing process than in the case that the user takes aim at the filling somewhat off-center. A specific problem is that in this case no information is available on the fact how much radiation energy the filling was exposed to. For example, a sufficient light power may be applied to portions of the filling, whereas other portions are not. The user up to now was not able to recognize, how far the filling had already cured. Finally an incorrect rating lead to an incompletely cured tooth filling.

In order to avoid the problems mentioned, according to the invention, the radiation sensor 120 is incorporated into the polymerization lamp 100 such that it is oriented into the same direction than the LED 110. Thus, the radiation sensor absorbs the light that is reflected by the filling and generates a signal based on the properties of the reflected light.

This signal can be used as information for the user. Preferably the signal of the radiation sensor 120 is used for determining the position.

In a first embodiment the radiation sensor 120 is embodied as a camera 120. The pictures taken by the camera 120 can be depicted on a display 130. This opens at first the possibility for the dentist or other users to make sure with a short glance on the display, if necessary, how the restoration result is represented optically, and even during the curing process. An experienced dentist typically recognizes the polymerization and can already determine by means of a short visual judgement, how far polymerization has progressed.

According to the invention it is particularly expedient in this conjunction that it is not necessary to insert an orange filter such that the full light power and the full spectrum are available for the judgement.

Instead of a charge coupled device (CCD) unit, the radiation sensor 120 can also simply be embodied as a photosensitive transistor. In this case the reflected light radiation strikes the transistor and increases or decreases the resistance of the transistor. The intensity of the reflected radiation thus influences the resistance of the phototransistor whose output signal is evaluated. With this solution it can be taken advantage of the fact that plastic material as filling material reflects light with a large portion of blue light with a higher intensity than the tooth itself that is to be restored. With a NPN-phototransistor, the light reflected by the filling material would produce a lower resistance than the light that is reflected by the tooth itself. The phototransistor can be interconnected in a measuring bridge for example, and by means of a corresponding evaluation circuit it can be assessed whether and to what extent the restoration material that is to be cured is impinged by the first radiation from the radiation source 110.

Also the camera 120 can easily be used for the assessment of the intensity of the reflected light radiation. The portions of the filling material that are impinged by the first radiation reflect the light radiation stronger such that brighter image areas are represented there by the camera 120. These brighter image areas can not only be depicted on a display but can also be evaluated by means of a corresponding evaluation circuit, in order to determine whether and to what extent the filling material is impinged by the first radiation.

In an alternative embodiment of the invention, the light radiation reflected by the object is evaluated and is compared to a first and a second reference value. If the light radiation that has been evaluated exceeds the first reference value, a signaling occurs that the position of the light curing apparatus has been correctly selected. If the light radiation reflected is below the first reference value or is above the second reference value, a suitable warning is generated, for example on the display 130, in order to inform the dentist that corresponding error conditions are present. A corresponding warning signal can be output acoustically.

In this case, the distance from the surface of the restoration material can be determined by performing a visual judgement on the display. Alternatively, the distance can be determined from the absolute quantity of the second radiation, since the intensity of the reflected radiation decreases with increasing distance from the surface that is impinged.

Alternatively or additionally, the radiation sensor 120 can also be used for determining the distance between polymerization lamp 100 and radiation sensor 120.

Preferably the radiation sensor 120 comprises a spectral sensitivity that forms a large overlap with the emission wavelength range of the LED 110. Thus, the necessity for employing filters is removed.

In a further preferred embodiment several radiation sensors 120 that are arranged in angles relative to one another, can be incorporated which are provided for determining the position and/or distance.

As discussed above, the apparatus comprises an adjustment device that preferably determines the distance between radiation sensor and object based on the second radiation. Based on this distance the adjustment device can adjust the system parameters of the apparatus. Preferably, those parameters are the emitted light power and the on-time of the radiation source. Since the amount of light of a radiation source that is absorbed by the object, changes more in dependence on the distance from the object that is irradiated, this approach is particularly efficient in the reduction of losses. This not only saves energy and avoids unnecessary heating of the apparatus, but also ensures that the amount of light necessary to effect polymerization, is supplied to the object.

Figure 2:
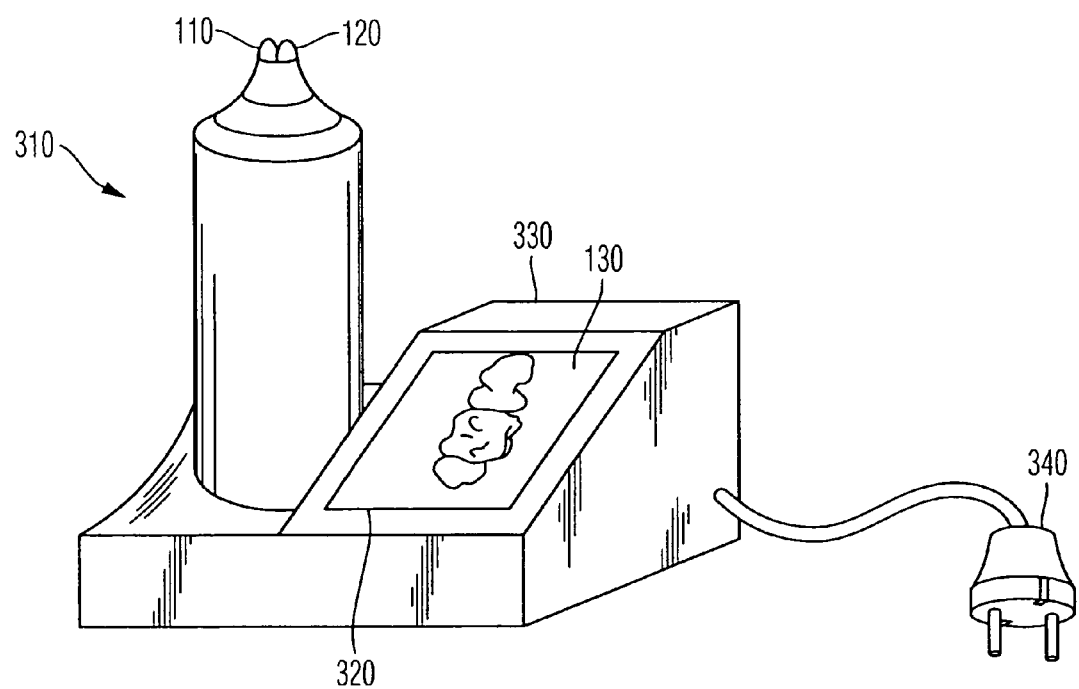
FIG. 2 shows a diagrammatic view of a second exemplary embodiment of the invention that comprises a charging station.

FIG. 2 shows a polymerization lamp 310 according to a second exemplary embodiment of the invention. Also in the second exemplary embodiment all functional features of the first exemplary embodiment can be integrated in the polymerization lamp 310. Thus the lamp 310 is provided with a radiation source 110 and a radiation sensor 120.

Further, the polymerization lamp 310 is accommodated in a charging device 330, which is provided with a display 130. This charging device 330 can be provided for charging a storage battery (not shown) of the polymerization lamp 310. In this case, the charging device 330 comprises a power supply 340 in the form of a plug that can be inserted or plugged into a plug receptacle of the public power supply network. Moreover, the charging device 330 also needs corresponding transformers in order to convert the voltage from the power supply network in a suitable charging voltage for the storage battery.

Further, the charging device 330 may also comprise a display 320 that is suitable for representing the position data and distance data that have been detected. These data can also be stored on a storage means (not shown) in the charging device 330.

Figure 3:
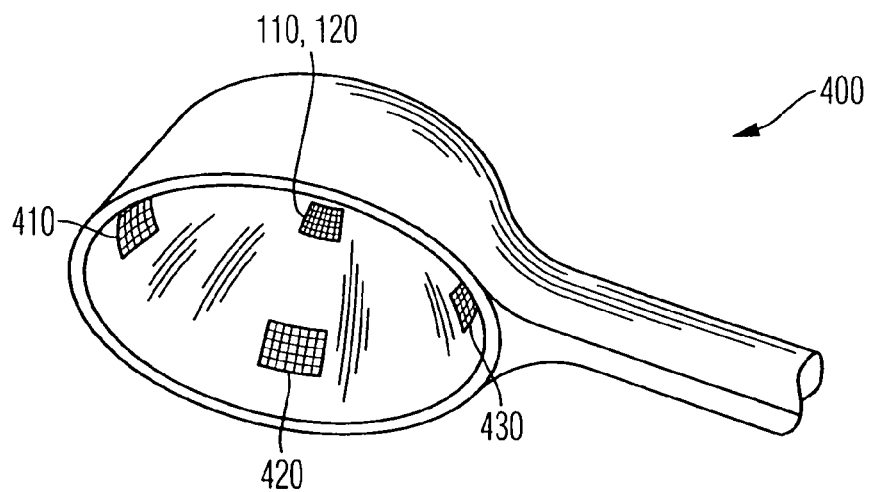
FIG. 3 shows a diagrammatic view of a third exemplary embodiment of the invention having hood shape.

FIG. 3 shows a multiple-sensor arrangement for the polymerization lamp according to a third exemplary embodiment of the invention. Accordingly, the LED 110 and the camera 120 are incorporated topside in the dome of a hood 400 that can be held above a natural or artificial tooth that is to be treated. The advantage of a hood of this kind is that the light from the LED 110 can be reflected from the walls of the hood in order to use it more efficiently for curing the filling material that is inserted into the tooth.

When using the hood 400, the sight of the filling material is covered during the curing process. By means of using the invention, however, it is now possible to effect the correct positioning and the correct distance between the LEDs 110, the hood and the filling material. In this respect, by means of the inventive position determination in this embodiment, by using the hood 400 the particular advantage can be achieved that an exactly defined and high-energy light radiation is supplied to the filling material at an exactly prescribed position.

In a further development of the hood 400 it comprises further cameras 410, 420, 430 at its inner edge. Those are substantially perpendicular to the camera 120 that is situated topside in the hood 400.

This arrangement of the cameras 410 to 430 enables the determination of the exact position of the hood 400 before switching on the radiation source 110. Thus, a visual judgement of the dental restoration is also possible, and the relative positioning and the visual configuration of the current situation can be represented in clearly enlarged form and is thus clearly apparent on the display.

Figure 4:
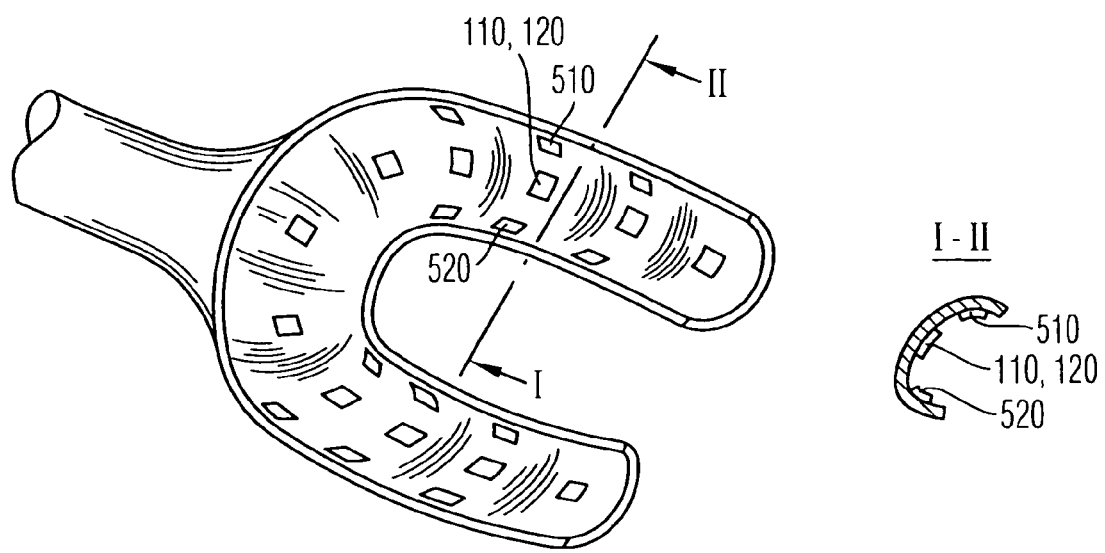
FIG. 4 shows a diagrammatic view of a fourth exemplary embodiment of the invention having U-shape in cross section, FIG. I-II being a sectional view taken along the line I-II in FIG. 4.

FIG. 4 shows a modified multiple arrangement of sensors and radiation sources for a polymerization lamp according to a fourth exemplary embodiment of the invention. In this embodiment at least one LED 110 and one camera 120 are installed in the top area of a hood 500, wherein the configuration of the hood 500 substantially corresponds to a vertically oriented U-shape and in this respect can be randomly positioned along a set of teeth. Preferably, the hood 500 comprises a plurality of LEDs 110 and cameras 120, wherein a pair of a LED 110 and a camera 120 can be positioned above a tooth.

Further cameras 510, 520 can be arranged at the inner edge of a dental arch shaped trough substantially perpendicular to the further cameras 120. This becomes apparent from the sectional representation I-II.

Figure 5:
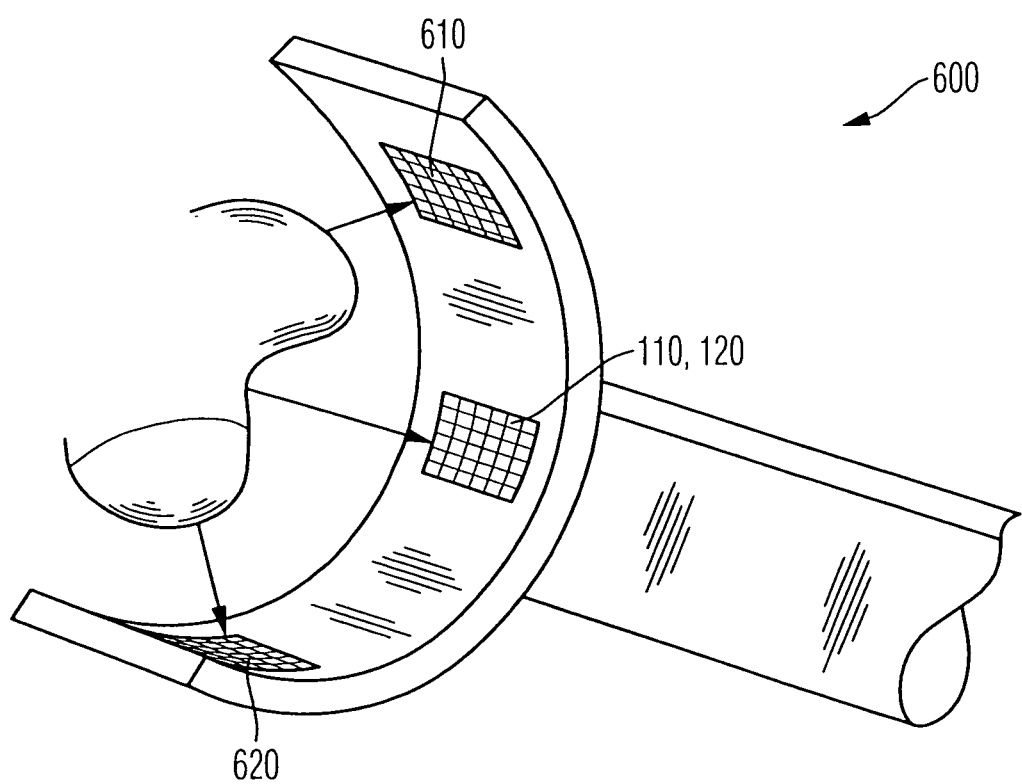
FIG. 5 shows a diagrammatic view of a fifth exemplary embodiment of the invention having arc shape.

In a further modified embodiment according to FIG. 5 a particularly formed multiple arrangement of LEDs 110 and sensors 120 are positioned at the center of a U-shaped hood 600. Additional camera 610, 620 are positioned at the edge. In this embodiment, the overall shape is formed such that it completely covers a dental set of natural or artificial teeth, and actually pretty tight, wherein the hood shape in the sectional view substantially extends semicircular over the pertaining tooth. In this conjunction, a plurality of light sources and sensors are mounted in random and suitable manner, and the light power emitted provides a uniform and bright illumination of the entire set of teeth.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. Apparatus for light-curing a dental object by means of a first radiation, the apparatus comprising:
   a housing;
   at least one radiation source mounted on the housing for emitting the first radiation;
   at least one radiation sensor mounted on the housing for measuring at least a second radiation, wherein the second radiation is the first radiation reflected by the object;
   wherein the second radiation is measured and compared to a reference value;
   wherein the apparatus comprises an output device for outputting perceptible information based on at least one measured value from the at least one radiation sensor;
   wherein the intensity and duration of the first radiation is controlled based on the measured value; and
   wherein if the reference value is met or exceeded, an output signal immediately signals that the radiation source is situated at an optimum position with respect to the dental object.

2. Apparatus as claimed in claim 1, wherein the radiation source is preferably formed by at least one laser diode or light-emitting diode LED, each LED having at least one LED-chip.

3. Apparatus as claimed in claim 1, wherein the radiation source emits a first radiation having a wavelength of 320 nm to 750 nm.

4. Apparatus as claimed in claim 1, wherein the radiation sensor is sensitive in a wavelength range of the first radiation emitted by the radiation source.

5. Apparatus as claimed in claim 1, wherein at least one of the radiation sensors is an image sensor, by means of which at least one picture of the object can be taken.

6. Apparatus as claimed in claim 1, wherein one radiation sensor is centrally located, and a plurality of other radiation sensors are provided that are arranged in spaced apart relationship in the same plane and/or in angles relative to the one radiation sensor.

7. Apparatus as claimed in claim 1, wherein the output device is embodied as a display that is arranged on the apparatus, and/or the output device outputs the information in a visual and/or acoustical and/or sensible manner.

8. Apparatus as claimed in claim 1, wherein the apparatus determines the distance to the reflection surface from the second radiation.

9. Method for curing an object, the method being characterized by the following steps:
   irradiating the dental object with a radiation source comprising high-energy light for curing a dental filling material;
   detecting a radiation that is reflected;
   measuring the radiation that is reflected;
   comparing the measured radiation to a reference value;
   detecting a relative position of the radiation source with respect to the dental object based on the measured light; and
   controlling the amount of radiation that is radiated from the radiation source; and
   wherein if the reference value is met or exceeded, an output signal immediately signals that the radiation source is situated at an optimum position with respect to the dental object.

* * * * *